United States Patent [19]

Dubczak et al.

[11] 4,221,865
[45] Sep. 9, 1980

[54] METHOD FOR DETERMINING ENDOTOXIN CONCENTRATION

[75] Inventors: John A. Dubczak, Chicago; Marlys E. Weary, Mount Prospect, both of Ill.

[73] Assignee: Baxter Travenol Laboratories, Inc., Deerfield, Ill.

[21] Appl. No.: 949,293

[22] Filed: Oct. 6, 1978

[51] Int. Cl.³ .................. G01N 21/47; C12Q 1/00
[52] U.S. Cl. ........................................... 435/4; 435/34
[58] Field of Search ............... 195/103.5 R, 103.54; 435/4, 34

[56] References Cited

U.S. PATENT DOCUMENTS

| | | | |
|---|---|---|---|
| 3,915,805 | 10/1975 | Levin | 195/103.5 R |
| 4,038,029 | 7/1977 | Teller et al. | 195/103.5 R |
| 4,148,869 | 4/1979 | Deaton | 195/103.5 A |

FOREIGN PATENT DOCUMENTS 1499846 2/1978 United Kingdom .

OTHER PUBLICATIONS

Niven, *Industrial Detergency*, pp. 44–45 (1955).
Putnam, *Advances in Protein Chemistry*, 4, 79–122, (1948).
Solum, *Throm. Diath. Haemorrh.*, 23, 170–181 (1970).
Young et al., *J. Clin. Invest.*, 51, 1790–1797, (1972).
Wildefeuer et al., *Applied Microbiology*, 28 (5), 867–871 (1974).
Solum, *Thrombosis Research*, 2, 55–70 (1973).
Gaffin, *Biorheology*, 13, 273–280 (1976).
Levin et al., *Throm. Diath. Haemorrh.*, 19, 186–197 (1968).

*Primary Examiner*—Esther M. Kepplinger
*Attorney, Agent, or Firm*—Paul C. Flattery; Lawrence W. Flynn; Max D. Hensley

[57] ABSTRACT

Improvements in the sensitivity and reproducibility of nephelometric endotoxin determinations using endotoxin-activated enzyme from Limulus amebocyte lysate are achieved by contacting endotoxin-coagulated lysate with an ionic surface active suspending agent, generally a mixture of detergent and suspending agent. Instrumentation improvements further enhance results.

31 Claims, 1 Drawing Figure

METHOD FOR DETERMINING ENDOTOXIN CONCENTRATION

BACKGROUND OF THE INVENTION

This invention relates to methods for the determination of endotoxin which use as their basis the endotoxin-activated enzymatic coagulation or block polymerization of certain proteins native to *Limulus polyphemus* blood cells. In particular, this invention relates to those methods in which the Limulus protein coagulation is followed by nephelometry.

The detection of endotoxin in solutions and in biological fluids has long been important in the economics of commercial production of therapeutic intravenous solutions, and in diagnosis and prognosis of human disease. This test has become an important factor in the cost of manufacturing parenteral solutions because the heretofore employed US Pharmacopeia method has required live rabbits and a complex and lengthy assay procedure.

Pyrogens of greatest commercial and disease importance are derived from gram negative bacteria. The terms "endotoxin", and "pyrogen" all refer to substances present in the cell walls of bacterial families such as Brucellaceae, Enterobacteriaceae, Pseudomonadaceae, and Spirillaceae. Striking examples of the role of these substances in disease are evident when it is realized that endotoxins are the primary cause of fever, diarrhea, and abortion in diseases such as typhoid, cholera, food poisoning, and Brucellosis. Development of endotoxemia from bacteria residing in the gastrointestinal tract is a prime cause of death in appendicitis or other conditions involving rupture of the colon.

Endotoxin assays using Limulus blood cell extracts or lystates have gained considerable acceptance. These assays make use of the phenomenon that an enzyme present in the Limulus lysate is activated by endotoxin, and that once activated the enzyme catalyzes a reaction with other lysate proteins to form a crosslinked or coagulated protein matrix or gel. Since the amount of gel is proportional to the amount of endotoxin originally present, endotoxin in unknown samples may be readily determined.

Originally, formation of a Limulus lysate clot after incubation for a fixed time in the presence of endotoxin was the signal used to measure endotoxin concentration. While this method is generally more sensitve than the US Pharmacopeia rabbit test and is simple to conduct, it is insensitive and subject to considerable variation and error. The test is insensitive because coagulation occurring at low endotoxin levels may be unapparent to visual examination. It is subject to error because of the difficulty in subjectively determining the point at which a clot occurs.

The sensitivity and reproducibility of the endotoxin assay have been improved by the use of various optical methods for detecting lysate precipitation. Some methods measure the reduction in the amount of light which is passed by a suspension of coagulated Limulus protein, i.e., they measure the absorbence or turbidity of the suspension. See for example U.S. Pat. Nos. 4,038,029 and 3,915,805, and Hollander et al., "Biochem, Med." 15: 28–33 (1976). Other workers have separated the coagulated protein from the reaction mixture, then chromogenically determined the total amount of coagulated protein. See the example in U.K. Patent Specification No. 1,499,846.

Another optical method for determining the extent of coagulation is nephelometry. This method is frequently described or suggested in other terms, e.g., determination of light scattering. For example, U.K. Patent Specification No. 1,499,846, U.S. Pat. No. 3,915,805 and Levin et al. ("Thromb. Diath. Haemorrh." 19: 186–197 [1968]) all speak in terms of Limulus protein coagulation detection by "light scattering". For the purposes of this application nephelometric methods for the detection of endotoxin are those in which a determination is made of the amount of light reflected by a solution or suspension of coagulated Limulus amebocyte protein at greater than 0° and less than 180° from the incident beam of light as a measure of the extent of coagulation of the protein by an endotoxin-activated Limulus amoebocyte enzyme.

Nephelometric methods have not found widespread acceptance in endotoxin detection. In part, this may be attributed to the poor results that have been reported to date when using this technique. The principal problems which are evident are those of sensitivity and reproducibility. Levin et al. (FIG. 8) reported no increase in light scattering of Limulus amebocyte lysate when contacted with 40 pg endotoxin/ml., and not until the endotoxin level was increased to 4000 pg/ml was a lethargic response noted. Similarly, U.S. Pat. No. 3,915,805 reported an endotoxin detection threshold of 500 pg/ml. Additionally, inspection of the specific results reported by this patentee discloses considerable irregularity in the plotted points, even at high endotoxin concentrations. While U.K. Patent Specification No. 1,499,846 and Hollander et al. disclose low endotoxin thresholds the results were obtained using optical density or turbidimetric procedures.

It is therefore an object of this invention to improve the sensitivity and reproducibility of nephelometric endotoxin assays.

It is an additional object of this invention to achieve the sensitivity of known endotoxin assays with a comparatively simple, inexpensive nephelometric procedure.

It is another object of this invention to provide compositions and nephelometer improvements to enhance the reproducibility and sensitivity of the prior nephelometric assays for endotoxin using Limulus protein.

These and other objects will be apparent from a consideration of this invention as a whole.

SUMMARY OF THE INVENTION

The above objects are achieved in a nephelometric method for determining endotoxin wherein a sample thought to contain endotoxin is contacted with an endotoxin-coagulable protein from Limulus amebocytes to form a reaction product containing coagulated protein, the improvement comprising contacting the reaction product with an ionic surface-active suspending agent. The ionic surface-active suspending agent is generally a dilute aqueous solution of an ionic detergent and a suspending agent. An additional improvement comprises determining the forward light scattering by said product of a substantially monochromatic incident light wavelength of greater than about 500 mu.

DESCRIPTION OF THE PREFERRED EMBODIMENTS

Figure 1:
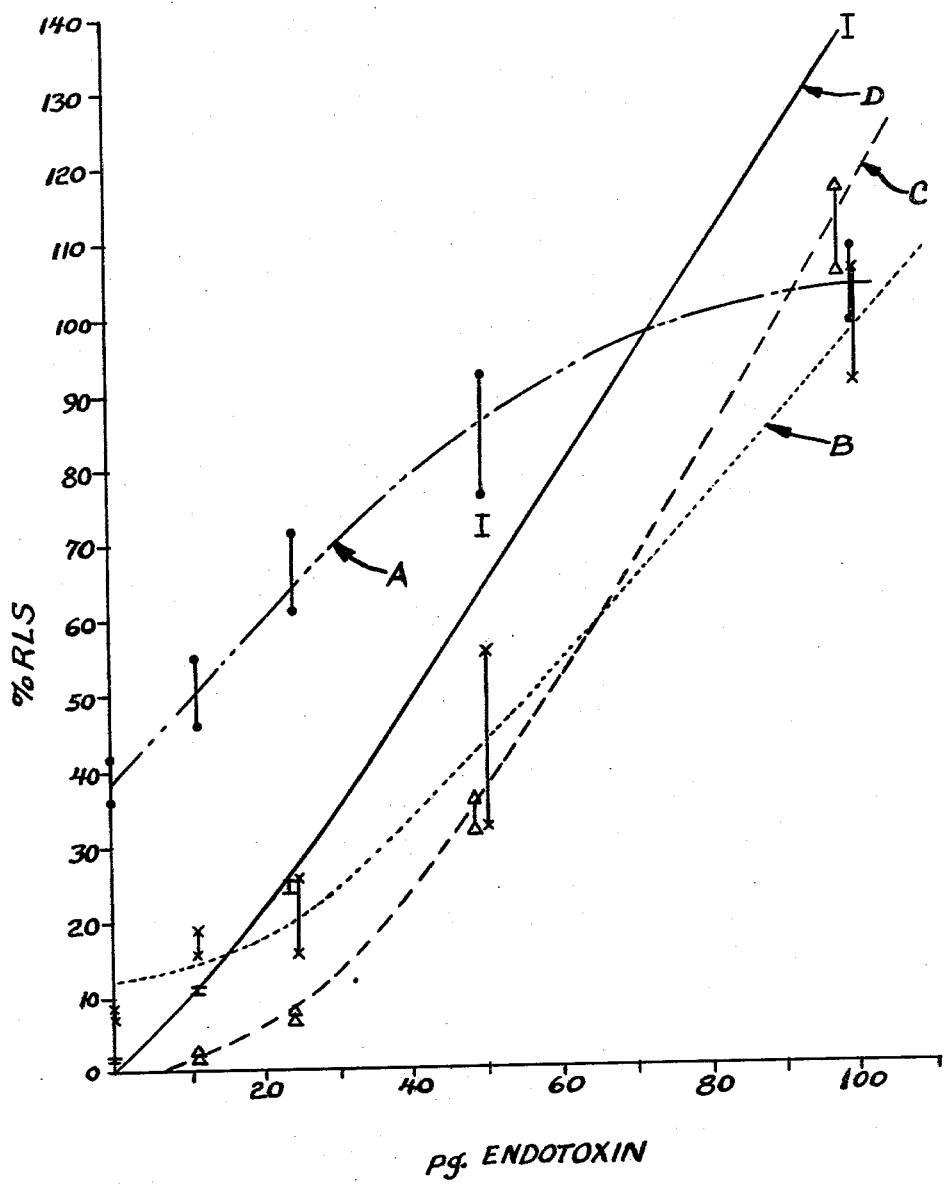
FIG. 1 demonstrates the improved sensitivity and reproducibility obtainable using the process of this invention. Curves A, B, C and D, respectively, delineate a nephelometric determination without the agent of this invention, with suspending agent only, with ionic detergent, and with both ionic detergent and suspending agent.

The ionic detergents for use in this invention will be cationic, anionic or amphoteric, and they all should exhibit certain general characteristics. First, their weight will generally range from about 150 to about 450. Second, it is convenient to select detergents which are capable of stopping the coagulation of Limulus protein; the use of such a detergent eliminates any need for a separate step in the method for stopping the reaction. Third, suitable detergents will preferably exhibit a high hydrophylic/lipophylic balance (HLB), generally greater than about 20 and most usually about from 30 to 40. The HLB for a selected detergent or mixture of detergents is generally available from the manufacturer of the detergent or may be readily calculated in accordance with known processes, e.g., as disclosed in Belgian Pat. No. 837,675.

Representative cationic detergents are the alkyl or aryl quaternary ammonium or quaternary pyridine salts such as cetyl trimethylammonium chloride, lauryl trimethylammonium bromide or benzyl triethylammonium chloride. Mixtures of such cationic detergents are within the scope of this invention.

Exemplary amphoteric detergents are the alkyl sulfonate or sulfate substituted quaternary ammonium salts having the general formulae:

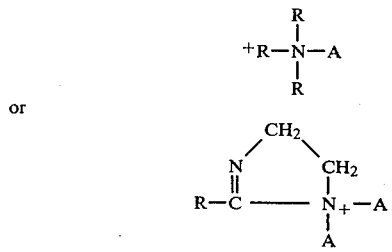

or wherein R is alkyl or aryl of from 1 to about 9 carbon atoms, and A is a carboxyl, sulfate or sulfonate-substituted alkyl radical of about from three to fourteen carbon atoms in which at least one A is sulfate or sulfonate-substituted. Generally, R is a short chain, normal alkyl such as methyl or ethyl. On the other hand, the A group alkyl radical is ordinarily a long chain, normal alkyl, for example nonyl or dodecyl. These detergents are well known and a number are commercially available. Again, mixtures may be used satisfactorily.

The preferred detergents of this invention are anionic. They are generally the sulfated or sulfonated derivatives of aryl alkanes, alkanes, fatty alcohols, olefins, monoglycerides, polyoxyethylenes, and succinates. Representative examples of each group are well known and commercially available.

The alkyl aryl and alkyl sulfonates are especially preferred. These compounds are saturated hydrocarbons ordinarily having a total of about from 8 to 20 carbon atoms. The alkyl aryl sulfonates contain a saturated hydrocarbon ring of from about 5 to about 8 carbon atoms which may be optionally hydroxyl or lower alkyl substituted, e.g., benzyl, toluyl, xylyl or hydroxyphenyl. In addition, the aryl group of the alkyl aryl sulfonates will be substituted with at least one sulfonated, short chain, normal alkyl having about from three to six carbon atoms. The sulfonyl group is generally located at the opposite end of this alkyl group from the aryl radical. A suitable alkyl aryl sulfonate is a salt of dodecyl benzyl sulfonate.

The alkyl sulfonates are the most preferred anionic detergents. Again, the alkyl group is ordinarily normal, terminally sulfonated and contains about from four to fifteen carbon atoms. The preferred detergent of this invention is sodium dodecyl sulfonate. The sodium dodecyl sulfonate is essentially free of sulfhydryl reducing agents such as mercaptoethanol.

The sulfonates or sulfate substituted detergents are generally employed as the alkali metal salts, preferably the sodium salts, while the cationic detergents are used as the halogen salts, e.g., chloride. The selection of ion is not critical so long as the resulting salt remains a water soluble detergent.

Various species of anionic detergents may be combined for use in this invention, as may different cationic and different amphoteric detergents. In fact, commerically available detergents such as sodium dodecyl sulfonate are often found contaminated with longer or shorter chain sulfonates, but such mixtures are entirely satisfactory. However, detergents of the three classes of anionic, cationic and amphoteric detergents should not be mixed as their charged radicals will tend to neutralize one another with a commensurate loss in detergent activity.

The amount of detergent to be used to achieve the unexpectedly improved results of this invention will vary depending upon the detergent selected and the sample to be determined. However, the amount should be sufficient to dissolve whatever coagulated Limulus protein one would expect to encounter with the test samples to be assayed under given reaction conditions. It is not necessary that so much detergent be added that the coagulated protein be converted into a true or molecular solution. Rather, a colloidal solution may be satisfactory so long as the protein aggregates are rendered substantially uniform by the detergent and there are no remaining macroscopic particles or clot fragments in the sample. The coagulated protein is considered to be dissolved when the coefficient of variation among replicates is below about 15%. The preferred average diameter of the dissolved protein is about from 0.1 to 0.4 microns. The quantitative amount of detergent to achieve the above goals is ordinarily at least about 0.05% by weight in the reaction product of the Limulus lysate and endotoxin-containing sample. The preferred amount when using sodium dodecyl sulfonate is about 0.16%. The detergent concentration has no real upper limit in achieving the objects of this invention, for after a threshhold is reached further additions of detergent yield no significant change in assay performance. For example, a concentration of 1.28% sodium dodecyl sulfonate in the reaction product can be used with an effect substantially equivalent to that achieved with 0.16%. Obviously, upper limits may be established by such considerations as detergent solubility, excessive foaming and nonspecific protein precipitation. However, these factors can be readily determined by the skilled artisan.

The suspending agent may be any emulsifying agent which has heretofore been employed to stabilize pharmaceutical or food emulsions and colloidal solutions. The suspending agent is generally a hydrophylic or hydrocolloid-forming organic macromolecular polymer having an average molecular weight of about from 1,000 to 20,000. Alternatively, and somewhat less desirably, the suspending agent may be a hydrocolloid-forming mineral such as one of the many commercially available clays, e.g., bentonite.

Native or synthetic organic polymers may be used as the suspending agent. However, it is preferred to use synthetic polymers as their supply is reliable and they may be secured in uniform lots. Suitable polymeric suspending agents are carboxymethyl cellulose, polyethylene glycol, methylcellulose, polyvinylpyrrolidone, polyvinyl alcohol, hydroxyethyl cellulose and carboxypolymethylene, with their alkali metal salts being most desirable. The use of suspending agent mixtures is within the scope of this invention. The preferred suspending agent is sodium carboxymethyl cellulose.

The concentration of suspending agent needed in the reaction product will be a function of the amount of coagulated Limulus protein expected, the effectiveness of the detergent in producing a uniform molecular or colloidal solution of coagulated protein, the molecular weight of the detergent, the presence of native suspending agents in the test sample and the nature of the suspending agent. Hence, limited routine experimentation may be necessary to determine the optimum concentration for the desired blank and standard curve slope. Generally, a satisfactory amount of suspending agent will yield a blank of less than about 15% relative light scatter. Suitable concentrations in the reaction product ordinarily should exceed about 0.01% by weight, but additional advantage is rarely obtained with a concentration greater than 0.3% by weight. The preferred concentration is about 0.06% by weight in the reaction product.

It should be understood that the properties of the detergent and the suspending agent will often overlap to a degree. For example, as the molecular weight of the detergent increases, emulsifying or colloidal suspending properties will appear. Similarly, either the introduction of charged moieties into the macromolecular suspending agent or increases in charge density will affect the degree of detergent activity exhibited by the agent. It is preferred to employ detergents and suspending agents that carry as little of the properties of the other as possible. However, it is within the scope of this invention to use ionic, surface active, suspending agents which essentially merge the characteristics of the detergent and suspending agent into a single polymer class. Generally, these bifunctional polymers are sulfonated or sulfated hydrocolloid-forming polymers such as cellulose sulfate, sulfonated polyoxyethylene or polystyrolsulfonate having a molecular weight of from about 500 to about 5000. A sufficient amount of these agents must be used to dissolve coagulated Limulus protein, including clotted protein, as described above in connection with monofunctional detergent. Again, optimal amounts can be determined by routine experimentation directed at achieving the performance desired for the detergent and suspending agent when supplied as discrete compounds. Usually the amount employed should be greater than about 0.05% by weight in the final reaction mixture, with the upper limit being largely a matter of discretion.

The ionic, surface active suspending agent may be supplied as a single aqueous solution containing bifunctional polymer or a mixture of detergent and suspending agent. However, the assay is more versatile if separate aqueous solutions of detergent and suspending agent are contacted with the reaction product separately. Since the detergent is preferably selected for its ability to stop the Limulus protein coagulation it should be contacted with the reaction product only after the reaction has proceeded to the desired stage of completion. On the other hand the suspending agent may be added to any point in the coagulation reaction, either before or after addition of detergent. If the suspending agent is added at the commencement of the reaction it is convenient to supply it as the magnesium or manganese salts. These ions are Limulus coagulation enzyme cofactors and their addition in this form can save a pipetting step. Nonetheless, it is preferred to add the suspending agent after the detergent has reached equilibrium with the coagulated Limulus protein. Addition of detergent may be optionally accompanied by the mechanical disruption of any clotted protein which has formed.

The solutions of detergent and suspending agent are ordinarily water solutions at a pH near neutrality which were passed through 0.45 $\mu$m and 1.2 $\mu$m filters, respectively, before use to remove large particulate contaminants that could interfere in the nephelometric determination. It is preferred that the solutions contain alkali metal ions, either by dissociation of detergent and suspending agent salts or by addition of extraneous ions in the form of inorganic salts.

The concentrations of detergent and suspending agent in the reagent may vary considerably as a matter of choice. Since it is disclosed above that comparatively low concentrations of detergent and suspending agent are effective, their concentrations in the added reagent may also be low. Solutions containing detergent about from 0.5% to 20% by weight and suspending agent about from 0.01% to about 3% by weight are satisfactory. For example, stock solutions of 1% sodium dodecyl sulfonate and 0.08% sodium carboxymethyl cellulose are sufficiently versatile to be used under most conditions. When using the small sample aliquots, e.g., 0.05 ml, made possible by the practice of this invention it is often necessary to increase the volume of the reaction product before it can be analyzed in commerical nephelometers, which generally require at least one ml. of sample. Thus dilute solutions of detergent and suspending agent perform the combined functions of increasing reaction product volume, dissolving coagulated Limulus protein, stabilizing the colloidal solution of the coagulated Limulus protein and quenching the endotoxin-activated Limulus enzyme responsible for the coagulation.

The foregoing improvements in the nephelometric determination of endotoxin are facilitated by the use of selected nephelometer features. For example, it is preferred that the incident or sample-illuminating light source of the nephelometer be substantially monochromatic. Ideally, a laser light source can be used for this purpose. The light source should be of a wavelength greater than about 500 mu, in the green to red portion of the visible spectrum, rather than in the blue range used heretofore (Levin et al., supra). A preferred wavelength is 632.8 nm. Finally, the photodetector should be mounted to detect forward light scatter, on the order of about 10° to 80° and preferably about 30°, rather than the 90° scatter conventionally measured. Forward light scatter is defined in terms of the angle distended between the scattered light and the incident beam measured on the side of the sample opposite the light source. A nephelometer having these features is commercially available from the Hyland Diagnostics Division of Travenol Laboratories, Inc., Costa Mesa, Calif.

While this invention has been described in terms of improvements to nephelometric procedures for the assay of endotoxin it is apparent that the improved replicate reproducibility achieved by the use of an ionic, surface active agent is of advantage in all Limulus endotoxin optical methods wherein light which is scattered or absorbed by the protein particles is detected. This includes not only nephelometric but turbidimetric or absorbance assays as well, e.g. determination of absorbance at 360 nm as measured opposite the incident light source illuminating the sample. For the purposes of this invention optical method are defined as nephelometric, turbidimetric or absorbance procedures.

The following specific examples are intended as illustrations but not limitations of the scope of the present invention.

EXAMPLE 1

This example demonstrates the preparation of a standard curve in a representative nephelometric assay for endotoxin, but without the use of detergent or suspending agent.

Lyophilized *Limulus polyphemus* blood cell lysate in pyrogen-free test tubes was prepared following the method of British Pat. No. 1,499,846. The lyophilized lysate was reconstituted by dissolution in 3.0 ml of 0.5 M $MgCl_2$. 0.1 ml aliquots of the lysate solution were then withdrawn and added to five sets of pyrogen-free test tubes, each set containing five tubes. 0.1 ml aliquots of 0, 12, 25, 50 and 100 pg/ml water solutions of *E. coli* 055.B5 endotoxin (Difco Laboratories) were added to the tubes to make up a set of 0, 12, 25, 50 and 100 pg/ml standards in five replicates each. The mixtures were incubated in a 37° C. water bath for 60 minutes. Then 1 ml of 0.9% NaCl was added and any clotted protein mechanically disrupted by rapid vortexing of each tube. The total light scattering of the suspension in each tube was measured by a Hyland PDQ ® nephelometer having a laser light source of 632.8 mu. The total elapsed time between adding endotoxin and conducting the nephelometric determination was approximately equal for each tube. The results are shown in curve A of FIG. 1 wherein the percent relative light scatter (%RLS) is plotted against concentration. The highest and lowest value secured with the five replicates at each endotoxin concentration were plotted and then joined with a bar. As can be seen from this curve, while a simple, unaided nephelometric endotoxin determination using the limulus system can be useful it nonetheless suffers from a number of defects. These include a very high blank or control, considerable replicate sample variation and overall curve nonlinearity. The elevated blank and curve nonlinearity adversely affect the assay sensitivity while the replicate sample variation and or nonreproducibility introduces error into the system.

EXAMPLE 2

The method of Example 1 was repeated except that the volumes of sample and lysate solution were reduced to 0.05 ml each and 1 ml of 0.08% sodium carboxymethylcellulose (CMC) suspending agent was added in place of the 0.9% NaCl solution. The sodium carboxymethylcellulose suspending agent was made by taking up commercially available CMC in saline to a concentration of 0.08% by weight and the solution passed through a 1.2 um Millipore filter disc. The results are shown in curve B of FIG. 1. As can be seen, the curve nonlinearity and replicate sample nonreproducibility still remain serious problems.

EXAMPLE 3

The method of Example 2 was repeated except that 0.2 ml of a 1.0% water solution of sodium dodecyl sulfate (SDS) was added in place of the 0.08% CMC solution. As can be seen from the results of this Example, graphed in curve C of FIG. 1 the detergent solution considerably reduced the replicate sample variation compared to assays either with or without CMC. However, nonlinearity of the standard curve persists when SDS is used alone.

EXAMPLE 4

This example demonstrates the surprising results obtained by use of both a detergent and a suspending agent in the nephelometric endotoxin assay. SDS was added as in Example 3, but within about 3 minutes thereafter 1 ml of the 0.08% CMC reagent was thoroughly mixed with the reaction mixture and the product assayed nephelometrically as above. The results are shown in curve D of FIG. 1. Surprisingly, it was found that the curve exhibits excellent linearity when compared to the results secured with SDS or CMC alone. This phenomenon demonstrates classic synergism because the linearity is clearly not an additive function of the effects of SDS and CMC. Further, while SDS used alone does reduce replicate variation, at elevated endotoxin concentrations CMC further reduces this variation. This is particularly surprising because the use of CMC alone demonstrates either no effect or an adverse effect on replicate variation at these endotoxin levels.

EXAMPLE 5

0.1 ml of test sample was added to 0.05 ml of Limulus lysate that had been reconstituted with 5 ml of 0.05 M Tris buffered 0.23% $MgCl_2$ to give a pH of 7.4 and an ionic strength of 0.07 moles/liter. This reaction mixture was incubated for 30 minutes at 37° C., after which 0.2 ml of 1.0% SDS and 1 ml of 0.8% CMC were sequentially added. The mixture was then vortexed and read in the nephelometer described in Example 1 which was standardized with a known endotoxin. Table 1 represents typical data obtained when known endotoxin concentrations were assayed using this optimum nephelometric system. As can be observed from the data obtained on three consecutive days, the assays are highly reproducible with an average slope of 1.55 and a coefficient of variation of 8.6% at 50 pg endotoxin/ml. %. Consistent data of this nature indicate that the nephelometric LAL assay system is a substantial improvement over existing test methods for the quantitation of endotoxin.

TABLE 1

| | | Endotoxin Conc (pg/ml) | | | | | |
|---|---|---|---|---|---|---|---|
| | Sample | 0 | 25 | 50 | 100 | Slope | $R^2$* |
| Day 1 | 1 | 1.1 | 17.9 | 68.3 | 153.2 | 1.583 | 0.9799 |
| | 2 | 4.7 | 25.6 | 72.7 | 150.5 | 1.505 | 0.9882 |
| | 3 | 0.4 | 18.2 | 69.5 | 157.3 | 1.631 | 0.9805 |
| Day 2 | 1 | 0.7 | 25.7 | 75.0 | 149.4 | 1.528 | 0.9921 |
| | 2 | 0.0 | 26.1 | 79.4 | 154.5 | 1.590 | 0.9912 |
| | 3 | 0.1 | 26.8 | 75.2 | 149.3 | 1.529 | 0.9938 |
| Day 3 | 1 | 1.7 | 31.1 | 80.2 | 151.8 | 1.533 | 0.9948 |
| | 2 | 1.3 | 33.2 | 86.4 | 150.2 | 1.519 | 0.9898 |
| | 3 | 0.0 | 29.7 | 87.3 | 151.14 | 1.555 | 0.9860 |
| Mean | | | 26.0 | 77.1 | 151.9 | 1.55 | 0.9879 |
| Standard Deviation | | | 5.2 | 6.7 | 2.6 | 0.04 | 0.0055 |

TABLE 1-continued

| Sample | Endotoxin Conc (pg/ml) | | | | Slope | R²* |
|---|---|---|---|---|---|---|
| | 0 | 25 | 50 | 100 | | |
| Coeff. of Variation | | 20% | 8.6% | 1.7% | 2.5% | 0.55% |

*R₂ = correlation coefficient indicating the linearity of the assay (1.0 suggests an ideal line).

The above examples and other specific information are contained herein for purposes of illustration only. Such alterations and modifications as would be apparent to those skilled in the art are deemed to fall within the scope and spirit of the invention, bearing in mind that the invention is defined only by the appended claims.

We claim:

1. In an optical method for determining endotoxin wherein a sample thought to contain endotoxin is contacted with an endotoxin-coagulable protein from Limulus amebocytes to form a reaction product which contains coagulated protein, the improvement comprising contacting the reaction product with a sufficient amount of an ionic surface active suspending agent to dissolve said coagulated protein.

2. The method of claim 1 wherein the surface-active suspending agent is a macromolecular detergent.

3. The method of claim 2 wherein the macromolecular detergent is an alkali metal salt of polystyrolsulfonate, cellulose sulfate or sulfonated polyoxyethylene.

4. The method of claim 2 wherein the macromolecular detergent has a molecular weight of about from 500 to 5,000.

5. In a nephelometric method for determining endotoxin wherein a sample thought to contain endotoxin is contacted with an endotoxin-coagulable protein from Limulus amebocytes to form a reaction product containing coagulated protein, the improvement comprising contacting the reaction product with a sufficient amount of an ionic detergent and a suspending agent to dissolve said coagulated protein.

6. The method of claim 5 wherein the detergent and suspending agent are mixed together and then contacted with the product.

7. The method of claim 6 wherein the detergent has an HLB of greater than about 30.

8. The method of claim 5 wherein the detergent is an alkyl or aryl sulfonate.

9. The method of claim 8 wherein the detergent is a sulfated or sulfonated fatty alcohol, olefin, monoglyceride or succinate.

10. The method of claim 5 wherein the detergent is cationic.

11. The method of claim 10 wherein the detergent is a quaternary ammonium salt.

12. The method of claim 5 wherein the detergent is amphoteric.

13. The method of claim 5 wherein the detergent has a molecular weight of about from 150 to 450.

14. The method of claim 5 wherein a sufficient amount of detergent is contacted with said product to yield at least about 0.05% of detergent by weight in said product.

15. The method of claim 8 wherein the detergent is sodium dodecyl sulfonate.

16. The method of claim 15 wherein a sufficient amount of sodium dodecyl sulfonate is contacted with said product to yield about 0.16% by weight of detergent by weight in said product.

17. The method of claim 5 wherein the suspending agent is a hydrocolloid-forming mineral.

18. The method of claim 17 wherein the suspending agent is bentonite.

19. The method of claim 5 wherein the suspending agent is a hydrocolloid-forming organic polymer.

20. The method of claim 19 wherein the suspending agent is alkali metal carboxymethyl cellulose, polyethylene glycol, methylcellulose, polyvinylpyrrolidone, polyvinyl alcohol, hydroxyethyl cellulose or carboxypolymethylene.

21. The method of claim 20 wherein the suspending agent is sodium carboxymethyl cellulose.

22. The method of claim 19 wherein the polymer has an average molecular weight of between about 1,000 and 20,000.

23. The method of claim 5 wherein an aqueous solution of the detergent is contacted with the reaction product.

24. The method of claim 23 wherein an aqueous solution of the suspending agent is contacted with the reaction product.

25. The method of claim 24 wherein the detergent solution is contacted with the reaction product prior to contact of the reaction product with suspending agent.

26. The method of claim 23 wherein the detergent is sodium dodecyl sulfonate and the aqueous solution is essentially free of sulfhydryl reducing agent.

27. The method of claim 5 wherein a sufficient amount of suspending agent is contacted with said product to yield at least about 0.01% of suspending agent by weight in said product.

28. The method of claim 21 wherein a sufficient amount of sodium carboxymethyl cellulose is contacted with said product to yield about 0.06% by weight of sodium carboxymethyl cellulose in said product.

29. The method of claim 5 wherein the suspending agent and detergent are contacted with the reaction product, respectively, before and after the endotoxin-coagulable protein has been allowed to coagulate.

30. In a nephelometric method for determining endotoxin wherein a sample thought to contain endotoxin is contacted with an endotoxin-coagulable protein from Limulus amebocytes to form a reaction product containing coagulated protein, the improvement comprising mechanically disrupting said coagulated protein in said product and contacting said disrupted protein with a sufficient amount of a suspending agent to yield a concentration of greater than about 0.01% by weight in said product, with the proviso that said product is not contacted with a detergent.

31. In an optical method for determining endotoxin wherein a sample thought to contain endotoxin is contacted with an endotoxin-coagulable protein from Limulus amebocytes to form a reaction product which contains coagulated protein, and then the light scattering or absorbence of a suspension of such reaction product determined, the improvement comprising contacting the reaction product with a sufficient amount of ionic surface active suspending agent to dissolve said coagulated protein.

* * * * *

UNITED STATES PATENT AND TRADEMARK OFFICE
CERTIFICATE OF CORRECTION

PATENT NO. : 4,221,865
DATED : September 9, 1980
INVENTOR(S) : Dubczak et al.

It is certified that error appears in the above-identified patent and that said Letters Patent are hereby corrected as shown below:

Col. 6, line 4, insert --reaction-- after coagulation.

Col. 6, line 7, --to-- should be --at--.

Signed and Sealed this

Eleventh Day of November 1980

[SEAL]

Attest:

SIDNEY A. DIAMOND

Attesting Officer

Commissioner of Patents and Trademarks